(12) United States Patent
Johansson

(10) Patent No.: US 10,994,113 B2
(45) Date of Patent: May 4, 2021

(54) TATTOO MACHINE CONTROL METHOD AND SYSTEM

(71) Applicant: Ink Machines Sweden AB, Växjö (SE)

(72) Inventor: Christian Johansson, Växjö (SE)

(73) Assignee: INK MACHINES SWEDEN AB, Växjö (SE)

( * ) Notice: Subject to any disclaimer, the term of this patent is extended or adjusted under 35 U.S.C. 154(b) by 137 days.

(21) Appl. No.: 16/093,669

(22) PCT Filed: Apr. 15, 2016

(86) PCT No.: PCT/EP2016/058412
§ 371 (c)(1),
(2) Date: Oct. 15, 2018

(87) PCT Pub. No.: WO2017/178070
PCT Pub. Date: Oct. 19, 2017

(65) Prior Publication Data
US 2019/0134372 A1    May 9, 2019

(51) Int. Cl.
*A61M 37/00* (2006.01)
(52) U.S. Cl.
CPC .... *A61M 37/0084* (2013.01); *A61M 37/0076* (2013.01); *A61M 2205/106* (2013.01); *A61M 2205/33* (2013.01)
(58) Field of Classification Search
CPC .......... A61M 37/0076; A61M 37/0084; A01K 11/005
See application file for complete search history.

(56) References Cited

U.S. PATENT DOCUMENTS

| 3,702,940 | A | * | 11/1972 | Stewart ................ | A61C 1/0007 307/326 |
| 4,900,252 | A | | 2/1990 | Liefke et al. | |
| 5,873,717 | A | * | 2/1999 | Behringer ............ | A61C 1/0015 433/101 |
| D613,572 | S | * | 4/2010 | Nielsen ........................... | D8/71 |

(Continued)

FOREIGN PATENT DOCUMENTS

| DE | 29919199 U1 | 1/2000 |
| DE | 102011120366 A1 | 6/2013 |

(Continued)

OTHER PUBLICATIONS

International Search Report and Written Opinion for PCT/EP2016/058412 dated Feb. 16, 2017, 11 pages.

(Continued)

*Primary Examiner* — Ryan J. Severson
(74) *Attorney, Agent, or Firm* — Brundidge & Stanger, P.C.

(57) ABSTRACT

A tattoo machine control system comprises a holding arrangement (1) for storing tattoo needle cartridges (3) for the moment not attached to a tattoo machine and a tattoo machine controller configured to 5 control a tattoo machine based on a tattoo machine setting. The holding arrangement (1) has a plurality of slots, each slot (13) being arranged for receiving a respective tattoo needle cartridge (3). The system is configured to maintain an association of a tattoo machine setting for said tattoo machine with a slot (13) 10 of said plurality of slots. The tattooing process is made more efficient.

20 Claims, 4 Drawing Sheets

(56) References Cited

U.S. PATENT DOCUMENTS

| | | | |
|---|---|---|---|
| 7,969,715 B2* | 6/2011 | Copeland | A61M 37/0076 361/679.01 |
| 8,228,666 B2* | 7/2012 | Rickard | A61M 37/0076 361/679.01 |
| 10,220,196 B2* | 3/2019 | Johansson | A61M 37/0076 |
| 10,449,346 B2* | 10/2019 | Juan | A61M 37/0076 |
| 2002/0069726 A1 | 6/2002 | Adler et al. | |
| 2005/0010236 A1 | 1/2005 | Frister | |
| 2006/0020283 A1 | 1/2006 | Lisec | |
| 2008/0254404 A1 | 10/2008 | Heraud | |
| 2010/0036317 A1 | 2/2010 | Oginski et al. | |
| 2010/0241151 A1* | 9/2010 | Rickard | A61M 37/0076 606/186 |
| 2012/0199150 A1* | 8/2012 | Le | B23B 39/24 132/75.8 |
| 2013/0123825 A1 | 5/2013 | Demjanenko | |
| 2013/0226211 A1* | 8/2013 | Xiao | A61M 37/0076 606/186 |
| 2015/0025561 A1 | 1/2015 | La Fontaine | |
| 2015/0202420 A1 | 7/2015 | Miller et al. | |
| 2016/0074057 A1 | 3/2016 | Jezierski | |
| 2016/0354592 A1* | 12/2016 | Juan | A61M 37/0076 |
| 2017/0021154 A1* | 1/2017 | Johansson | A61M 37/0076 |
| 2018/0028799 A1* | 2/2018 | Hofung | H01H 47/001 |
| 2019/0134371 A1* | 5/2019 | Johansson | A61M 37/0076 |
| 2019/0134372 A1* | 5/2019 | Johansson | A61M 37/0084 |
| 2020/0086103 A1* | 3/2020 | Juan | A61M 37/0076 |

FOREIGN PATENT DOCUMENTS

| | | |
|---|---|---|
| EP | 2826518 A1 | 1/2015 |
| GB | 2488323 A | 8/2012 |

OTHER PUBLICATIONS

International Search Report and Written Opinion for PCT/EP2016/058411 dated Mar. 21, 2017, 17 pages.

* cited by examiner

TATTOO MACHINE CONTROL METHOD AND SYSTEM

CROSS-REFERENCE TO RELATED APPLICATION

This Application is the National Stage filing under 35 U.S.C. § 371 of PCT Application Ser. No. PCT/EP2016/058412 filed on Apr. 15, 2016. The disclosure of which is hereby incorporated herein by reference in its entirety.

TECHNICAL FIELD

The present invention relates to a tattoo machine control method and system and to a tattoo needle cartridge.

BACKGROUND

Tattooing may be facilitated by the needles being packaged and used as part of cartridges. The document EP1872823 B1 describes a hand-held tattooing machine and such a cartridge.

There is always a need to make the tattooing process more efficient.

SUMMARY

To this end, there is provided a tattoo machine control method, a tattoo machine control system, and a tattoo needle cartridge, each of which may separately solve or at least mitigate the problem stated above.

The tattoo machine control method comprises maintaining an association between a tattoo machine setting and a slot in a plurality of slots for storing tattoo needle cartridges. An advantage thereof is that the tattooing process is made more efficient, and the risk of making mistakes during it is reduced, since a setting appropriate for a cartridge stored in that slot is remembered by the system and thus may be kept when the cartridge is not in use. Moreover, a setting appropriate for a specific cartridge can be maintained without using cartridge identification means. In particular, no identification means are needed between the cartridge and the tattoo machine.

Furthermore, an association of a plurality of tattoo machine settings with respective slots in a plurality of slots for storing tattoo needle cartridges may be maintained. An advantage thereof is that the risk of making mistakes when using several cartridges during one tattooing session is reduced, since the setting associated with a particular cartridge/slot can easily be obtained.

The setting may be a voltage and/or current setting for a tattoo machine.

The removal and/or attachment of a tattoo needle cartridge from a slot may be automatically detected, for example with an inductive presence sensor, such as a Hall effect sensor. An advantage thereof is that the setting can be selected or transferred automatically for use with the tattoo machine. Thus, the user will not need to manually indicate to the system that a cartridge has been removed, reducing the risk of making mistakes.

Upon indication of the removal of a tattoo needle cartridge from a slot, the method may comprise selecting a tattoo machine setting associated with said slot for use by a tattoo machine. The indication may be manual by the user or based on automatic detection. If an association between a plurality of tattoo machine settings with respective slots is maintained, there is a reduced risk of confusing the settings for different cartridges.

User input may be received for modifying a tattoo machine setting, when using a corresponding cartridge with a tattoo machine. The cartridge may be one that was previously removed from a slot, whereupon a setting associated with that slot was selected for use by a tattoo machine. An advantage hereof is that a setting may be adjusted according to need during the tattooing session.

A slot from which a tattoo needle cartridge was last removed may be indicated, for example visually, for example with an LED. An advantage thereof is a reduced risk by the user of confusing different cartridges.

Upon attachment of a tattoo needle cartridge to a slot, for example after detection of that attachment, a tattoo machine setting, preferably one most recently used by a tattoo machine, may be associated with that slot. An advantage thereof is that if a setting has been modified while a cartridge has been in use, the new setting can be kept. Another advantage is that if the user attaches a cartridge to another slot than the one it was last attached to, the appropriate setting will be associated with the new slot.

The presence of a tattoo needle cartridge in a slot may be indicated, for example visually, for example with an LED. An advantage thereof is that the user receives confirmation that the presence of a cartridge in a slot has been detected.

A tattoo needle cartridge comprising a magnet may be attached and/or detached to/from a slot. An advantage thereof is that no moving parts need to be exposed, allowing surfaces more easily to be cleaned, thereby improving hygiene. Another advantage is that the maneuver can be performed using one hand.

The tattoo machine control system comprises a holding arrangement for storing tattoo needle cartridges, where those cartridges for the moment are not attached to a tattoo machine. It further comprises a tattoo machine controller, which is configured to control a tattoo machine based on a tattoo machine setting. The holding arrangement has a plurality of slots, where each slot is arranged for receiving a respective tattoo needle cartridge. The system is configured to maintain an association of a tattoo machine setting for said tattoo machine with a slot. An advantage thereof is that the tattooing process is made more efficient, and the risk of making mistakes during it is reduced, since a setting appropriate for a cartridge stored in that slot is managed by the system. The setting may be saved when the cartridge in the slot to which it is associated isn't used in a tattoo machine. Moreover, a setting appropriate for a specific cartridge can be maintained without using cartridge identification means. In particular, no identification means are needed between the cartridge and the tattoo machine.

The system may be configured to maintain an association of a plurality of tattoo machine settings with respective slots. An advantage thereof is that the risk of making mistakes when using several cartridges during one tattooing session is reduced.

The tattoo machine setting may comprise a voltage and/or a current setting.

The system may further comprise a detector for automatically detecting the removal and/or attachment of a tattoo needle cartridge from/to a slot. An advantage thereof is that the user will not need to manually indicate to the system that a cartridge has been removed, reducing the risk of making mistakes.

The detector may comprise an inductive presence sensor, such as a Hall effect sensor.

The system may further be configured to, upon the detector detecting the removal of a tattoo needle cartridge from a slot, select a tattoo machine setting associated with that slot for use by the tattoo machine. An advantage thereof is that the setting can be selected or transferred automatically for use with the tattoo machine, removing the need to enter it manually. If an association between a plurality of tattoo machine settings with respective slots is maintained, there is a reduced risk of confusing the settings for different cartridges.

The system may further comprise a user interface to allow a user to modify a tattoo machine setting at will by interacting with the controller. An advantage hereof is that a setting may be adjusted according to need during the tattooing session.

The system may further comprise an indicator, for example a visual indicator, preferably an LED, which is configured to indicate the slot from which a tattoo needle cartridge was last removed. An advantage thereof is a reduced risk by the user of confusing different cartridges.

The system may further be configured to, when the detector has detected the attachment of a tattoo needle cartridge to a slot, associate a tattoo machine setting used by the controller with that slot. The setting is preferably one last used by the controller. An advantage thereof is that if a setting has been modified while a cartridge has been in use, the new setting can be kept. Another advantage is that if the user attaches a cartridge to another slot than the one it was last attached to, the appropriate setting will be associated with the new slot.

The system may further comprise an indicator, for example a visual indicator, preferably an LED, which is configured to indicate the presence of a cartridge in a slot. An advantage thereof is that the user receives confirmation that the presence of a cartridge in a slot has been detected.

Each slot may be provided with a magnet for holding a respective cartridge. An advantage thereof is that cartridges may be attached using magnets, meaning that no moving parts need to be exposed, allowing surfaces more easily to be cleaned, thereby improving hygiene. In addition this allows the operation of attaching and detaching cartridges to be performed using one hand.

The holding arrangement may comprise a rail provided with slots. An advantage thereof is a compact construction that is easy to use.

The holding arrangement may comprise a stand, which preferably has a substantially C-shaped cross-section. An advantage a C-shaped cross-section is that the stand also functions as a protective cover for a table on which it stands, should any fluid drip from cartridges attached to the holding arrangement.

The stand may at least partially be made from non-magnetic material, such as non-magnetic sheet metal. An advantage thereof is that magnetic cartridges will not attach to the stand, but only to the slots. Then, the rail may be attached on a first side of the stand so that the slots can be accessed from a second side of the stand, the magnetic field extending through the non-magnetic material. If the non-magnetic material is non-magnetic sheet metal, a further advantage is that the slots will have a hygienic and durable flat metallic surface.

The control system may comprise a tattoo machine controller unit separate from the holding arrangement. An advantage thereof is that it allows placing of each component at the most ergonomic and hygienic location. For example, the control unit can be brought close to the tattooing machine.

The controller unit and the holding arrangement may be configured to communicate wirelessly.

The controller unit and the holding arrangement may be configured to use wired communication.

The holding arrangement may be configured to be attached to an edge of a table. An advantage thereof is that there is no need for a stand.

The holding arrangement may be configured to hold tattoo needle cartridges with their needle nozzles pointing substantially downwards. An advantage thereof is that any ink in a cartridge will be maintained in a lower or lowermost portion of the cartridge. In addition, body fluids are prevented from flowing towards the upper end of a cartridge, from which the needles are driven, when the cartridge has not been used for some time.

The holding arrangement may be configured to hold tattoo needle cartridges at an end of the cartridges opposite to their needle nozzles. An advantage thereof is that the cartridge will be held at the end less exposed to body fluids, thereby facilitating keeping the holding arrangement clean.

The tattoo needle cartridge is adapted for use with the tattoo machine control method and/or the tattoo machine control system. It comprises a magnet configured to attach to a slot thereof. An advantage of using a cartridge with a magnet is that is can easily be attached to a slot without exposing any moving parts, allowing surfaces more easily to be cleaned, thereby improving hygiene.

The cartridge may be configured to fit to a slot, where the interface between the cartridge and the slot is a flat surface. Advantages thereof are increased hygiene and a reliable connection between cartridge and slot.

The magnet may be a drive magnet connected to a tattoo needle. An advantage thereof is that the same device, i.e. magnet, may be used both for driving the needle and to attach the cartridge to a holding arrangement.

The cartridge may comprise a rigid back wall. An advantage thereof is that fluids cannot escape the cartridge at the end which connects to a holding arrangement.

The cartridge may be configured for radial magnetic engagement with a tattoo machine drive unit. An advantage thereof is a reliable driving of the needle and hygiene, since no moving parts need to be accessed from outside.

BRIEF DESCRIPTION OF THE DRAWINGS

These and other aspects of the invention will now be described in more detail, with reference to embodiments of the invention.

DETAILED DESCRIPTION

A tattooing artist may need to use several different types of needles during a tattooing session. The exchange of needles may be time-consuming and complicated. If needles cannot easily be changed during the session, several tattoo machines using different types of needles may need to be used. This is often addressed by using tattoo machines which use needle cartridges. However, different settings for the tattoo machine may be needed when using different types of needles and needle cartridges, so that there is still a need for using separate machines.

Each needle type may need different settings or operating parameters of the tattoo machine, such as voltage and/or current supplied by a power supply connected to the tattoo machine. Those operating setting may depend on the type of needle, but also on the personal taste of the tattooing artist. It may therefore be necessary to readjust the settings for each type of needle used during a session.

In general, there is always a need to make the tattooing process more efficient and to reduce the risk of making mistakes during it.

Figure 1:
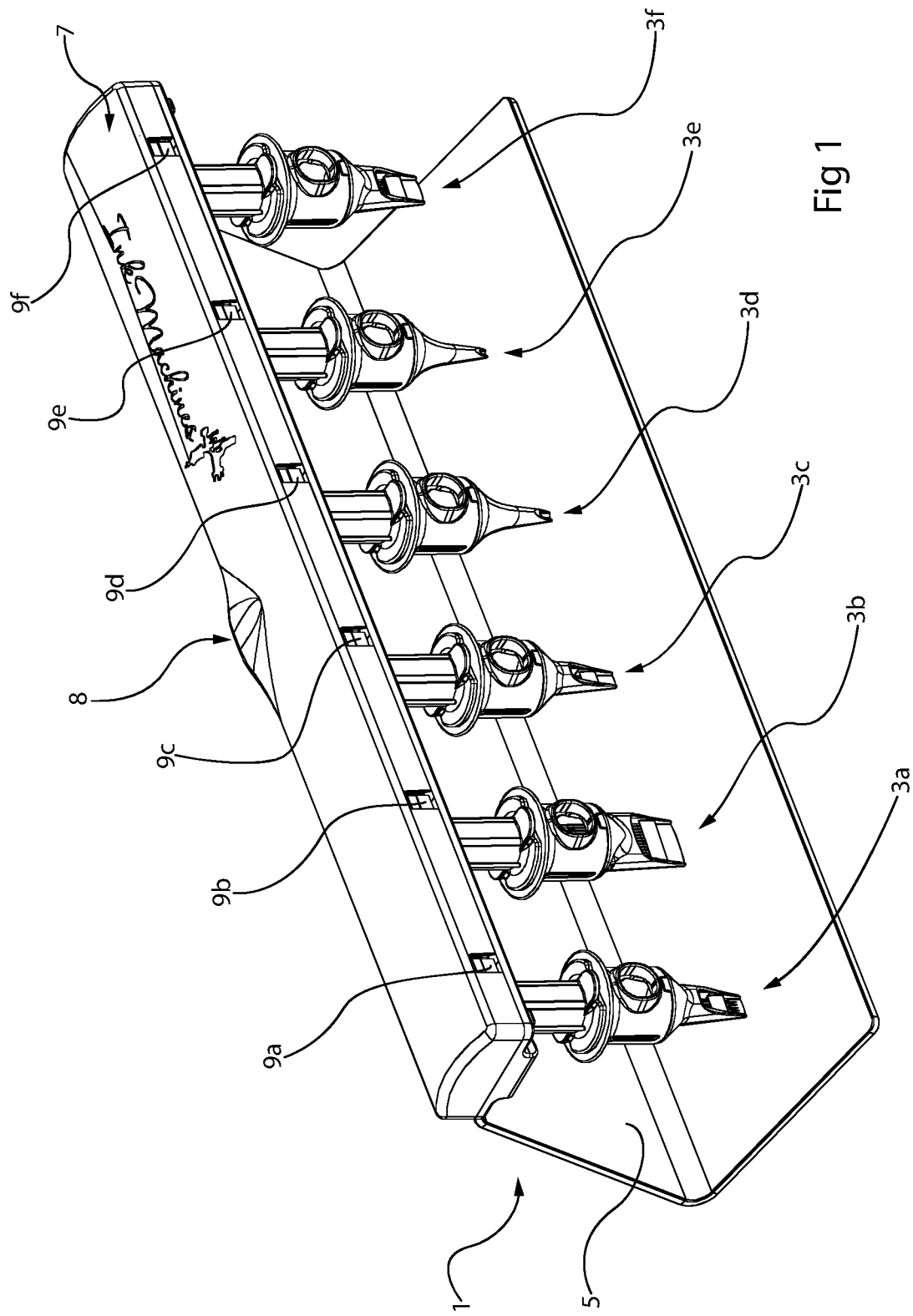
FIG. 1 is a perspective drawing showing a holding arrangement and a number of cartridges, seen from above.

FIG. 1 shows a holding arrangement 1, seen from above. The holding arrangement 1 comprises a stand 5 and a rail 7 attached to the stand 5. The holding arrangement 1 may be used to store needles to be used during a tattooing session. By way of example, six tattoo needle cartridges 3a-f are shown attached to the holding arrangement 1. Tattoo needle cartridges 3 may be of different kinds, comprising different numbers and/or types of needles.

The rail 7 has an elongated shape. On a long edge of the rail 7 facing the user, there is a first set of visual indicators 9a-f. In this particular embodiment, those visual indicators 9a-f are green LEDs.

The stand 5 is made from non-magnetic sheet metal, such as aluminum. An advantage thereof is that magnets present in the rail 7 may hold a cartridge 3 through the material of the stand 5. The stand 5 provides a flat, rugged surface for a cartridge 3 to be attached to.

Figure 2:
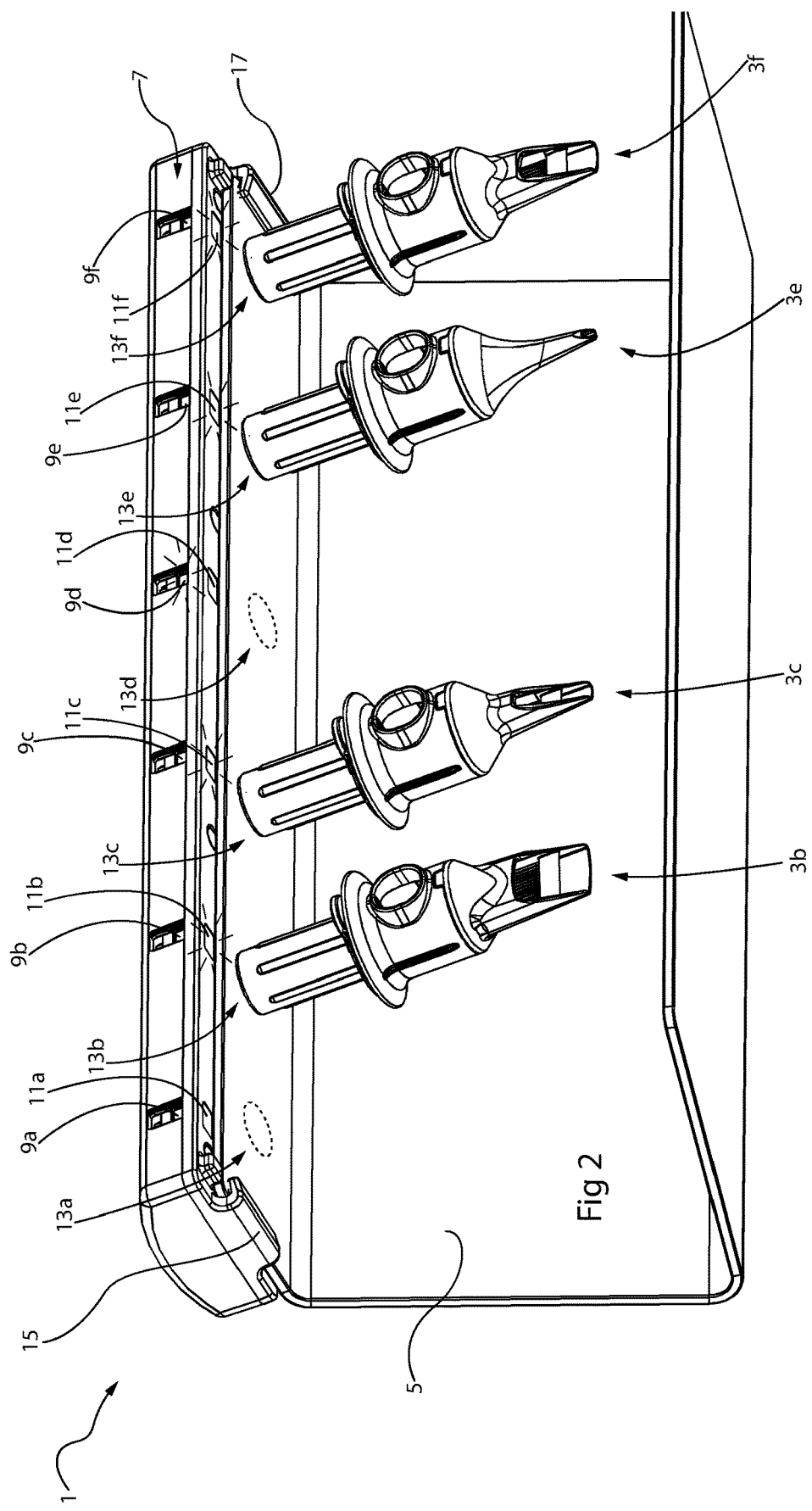
FIG. 2 is a perspective drawing showing the holding arrangement and a different number of cartridges, seen from below.

FIG. 2 shows the same holding arrangement 1, seen from below. The rail 7 is clamped to the stand 5 using two clamping structures 15, 17, each located at a respective short edge of a lower surface of the rail 7. The holding arrangement 1 provides predefined slots 13a-f, to/from which tattoo needle cartridges 3 may repeatedly be attached and/or removed. Each slot 13 has a neodymium slot magnet 25 (see FIG. 3) defining an attachment position for holding a respective cartridge 3 and a Hall effect sensor 37 for detecting the presence of a cartridge 3. By way of example, counted from the left, the first 13a and fourth 13d slots are unoccupied and the second 13b, third 13c, fifth 13e, and sixth 13f slot have respective cartridges 3b, 3c, 3e, 3f attached.

In addition to the first set of visual indicators 9a-f discussed above, a second set of visual indicators 11a-f are located on a lower surface of the rail 7. The first set of indicators 9a-f may use one color and the second set of indicators another color 11a-f. By way of example, the second set of visual indicators 11a-f may be red LEDs. Each of these visual indicators indicates the presence of a cartridge 3 in its respective slot 13, as detected by the respective Hall effect sensor. In the example illustrated in FIG. 2, the indicators 11b,c,e,f, corresponding to slots 13b,c,e,f where cartridges 3b,c,e,f are attached, are lit up, while the indicators 13a,d corresponding to slots 13a,d to which no cartridges 3 are attached are not lit up.

Figure 3:
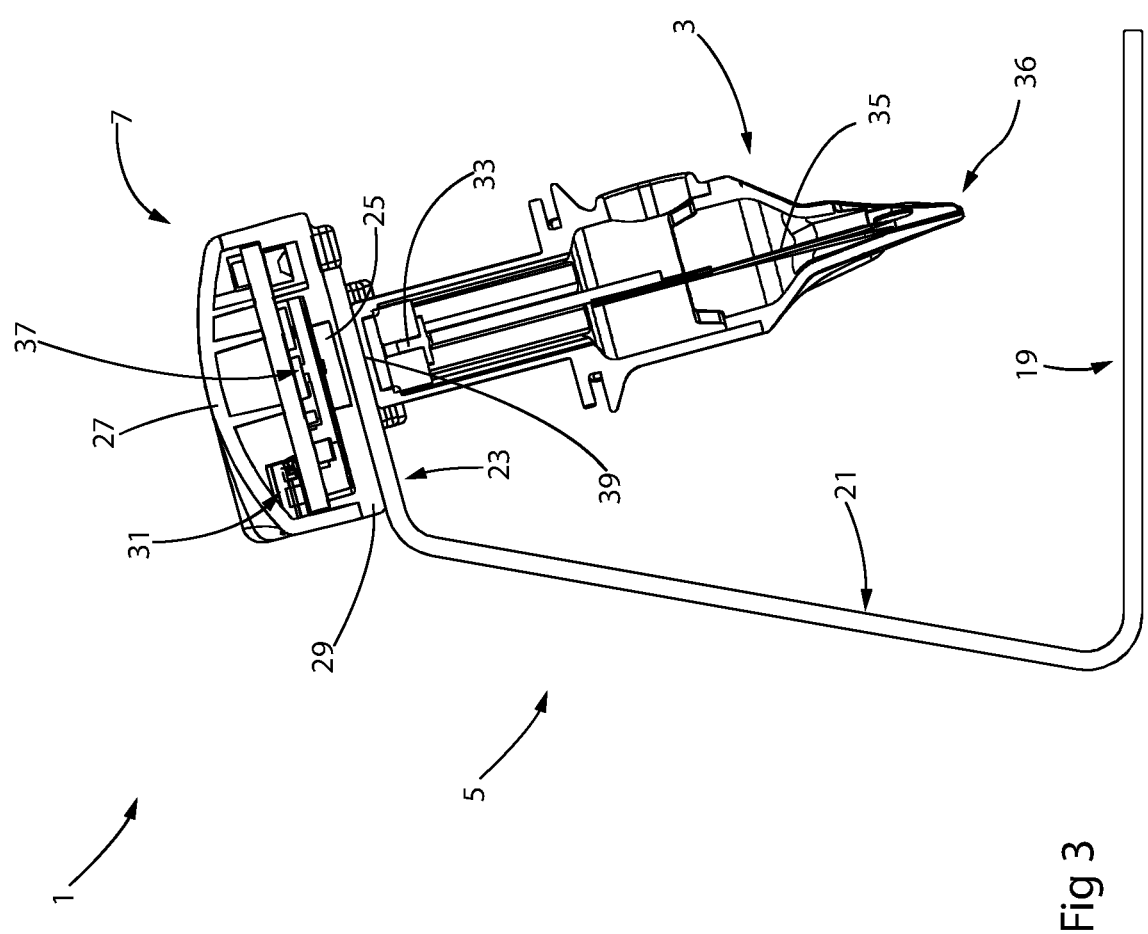
FIG. 3 is a cross-sectional view of the holding arrangement and a cartridge.

FIG. 3 shows a cross section of the holding arrangement 1 and a cartridge 3. The stand 5 is substantially C shaped, with three substantially flat sections, viz., a lower part 19 parallel to a supporting surface such as a table (not shown), a middle part 21 extending upwards from the supporting surface at an angle that may be oblique, and an upper part 23 on which the rail 7 is attached. The plane upper part 23 as illustrated is at a small oblique angle with respect to the lower parts, but it may also be horizontal.

The rail 7 comprises an upper cover 27 and a lower cover 29. A neodymium slot magnet 25 is located in a recess of the lower cover 29. A connector 31 is located near the back of the rail 7. The connector serves the purpose of communication with a controller 43 (cf. FIG. 4). It may be a micro-USB connector.

The tattoo needle cartridge 3 comprises a neodymium cartridge magnet 33 suitable for attaching the cartridge 3 to a slot of the holding arrangement 1. The cartridge magnet 33 may also be used as a drive magnet by a tattoo machine 41 (cf. FIG. 4) for driving a needle or several needles 35. The cartridge 3 has a rigid flat back wall 39 suitable for mating and forming an interface with the flat smooth surface of the stand 5 at a slot 13. The cartridge 3 is configured so that a magnet (not shown) of a tattoo machine can engage radially with the cartridge magnet 33. When the needles 35 are driven as described, they describe a back-and-forth motion, periodically extending out of the needle nozzle of the cartridge 3.

Figure 4:
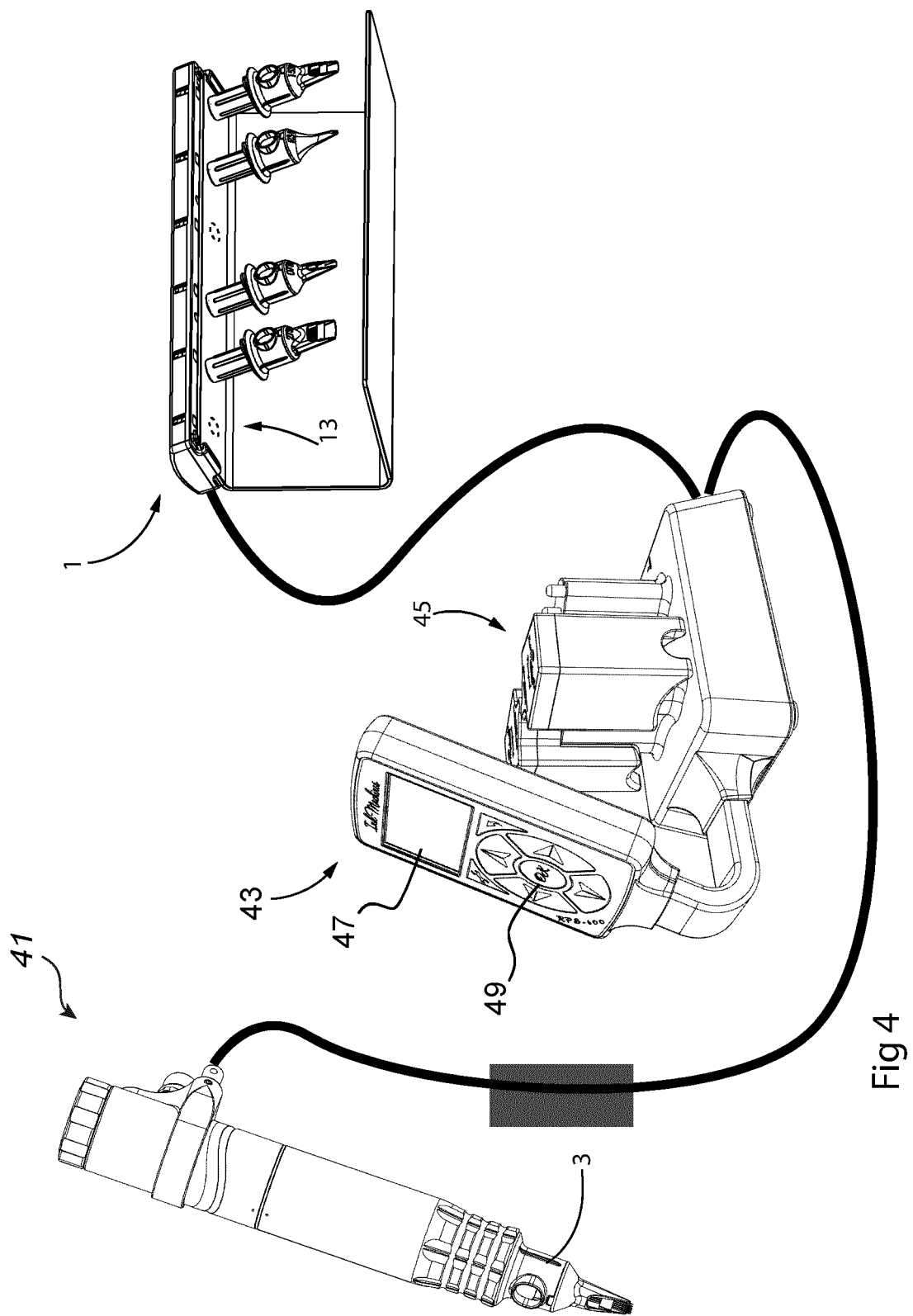
FIG. 4 is a perspective view of holding arrangement and a separate control unit.

FIG. 4 shows a tattoo machine 41, a controller 43 and a holding arrangement 1. The holding arrangement 1 is connected to the controller 43 and forms together with the holding arrangement 1 a tattoo machine control system. As shown in the figure, the controller 43 may be a controller unit 43 separate from the holding arrangement 1, but it may also be integrated with the holding arrangement 1. The separate controller unit 43 may communicate with the holding arrangement 1 either wirelessly or through wired means. In FIG. 4 a wired configuration is illustrated. A tattoo machine 41 is connected to and driven by a power supply 45, which is either part of or communicating with the controller unit 43. The driving voltage of the power supply may be varied according to the needs of the user, who may adjust it though a user interface that for example may comprise a display 47 and a keys 49. The driving voltage may be adapted to a specific type of needle and/or the personal tastes of a tattooing artist.

Such a voltage setting may be associated with one or more of the slots of the holding arrangement 1. Such an association may for example be made in some storage means present in the controller 43. Such storage means may for example be electronic storage means, such as digital storage means, such as flash memory or random access memory (RAM). Furthermore, there exists controlling electronics to manage the storage means and user interface 47, 49. The storage means and/or the controlling electronics may be located in the controller 43 and/or in the holding arrangement 1.

When the user removes a cartridge 3 from a slot 13, the removal is detected by the Hall sensor and communicated to the controller 43. The setting associated with that slot 13 is identified and selected by the controller 43 for use by the tattoo machine 41. If no setting has yet been associated with that slot, a default value is used. To indicate the slot 13 from which a cartridge 3 was last removed and/or the slot 13 from which a setting was last selected for use with by the controller 43, the corresponding green LED 11 is lit. This indicates a home slot of the presently used cartridge 3, aiding the user. By way of example, in FIG. 2 the fourth LED from the left 11d is lit to indicate that the voltage setting associated with the fourth slot from the left 13d was last selected for use by the controller 43, when a cartridge 3 was removed from that slot 13d for use in the tattoo machine 41.

After a cartridge 3 has been removed from the holding arrangement 1 and a voltage setting associated with a slot 13 has been selected for use by the controller 43, the user may modify that setting by interacting with the controller 43, when using the corresponding cartridge 3 with the tattoo machine 41. When a cartridge 3 is attached or re-attached to a slot 13 of the holding arrangement 1, the voltage setting currently used by the tattoo machine 41 is associated with that slot 13. This functionality may be present in one slot 13, a plurality of slots 13, or with all slots 13 of the holding arrangement 1.

The present disclosure is not limited by the above example, and may be varied and altered in different way within the scope of the appended claims.

For example, the association of a setting with a slot may use a display which displays the content of a setting stored in memory. The slot may have a keypad or other user interface to adjust the setting associated with the slot. Transfer of such a setting for use by a tattoo machine may be manual instead of automatic.

While a configuration wherein the holding arrangement 1 comprises a stand 5 and a rail 7 was described above, the holding arrangement 1 may comprise a single rail 7 without a stand, for example to be attached to an edge of a table. Separate holders for each slot are equally possible.

Slots 13 may, instead of being predefined by location, be based on the detection of the presence and location of a cartridge 3.

It is equally possible to use a camera and image analysis means to detect the presence and/or location of a cartridge.

A tattoo machine setting may comprise a frequency setting, a current setting, a voltage setting, an RPM setting, and/or any other setting to be used for controlling a tattoo machine.

The invention claimed is:

1. A tattoo machine control method implemented by a tattoo machine control system, the method comprising
   storing, by a holding arrangement, tattoo needle cartridges, wherein said holding arrangement has a plurality of slots, each slot being arranged for receiving a respective tattoo needle cartridge;
   controlling, by a tattoo machine controller, a tattoo machine based on a tattoo machine setting; and
   storing, by said tattoo machine control system, a plurality of tattoo machine settings for a tattoo machine, wherein each tattoo machine setting of said plurality of tattoo machine settings corresponds to each respective slot of the plurality of slots for storing tattoo needle cartridges.

2. The method according to claim 1, further comprising automatically detecting removal or attachment of a tattoo needle cartridge from/to said slot of said plurality of slots.

3. The method according to claim 1, further comprising upon indication of the removal of a tattoo needle cartridge from said slot of said plurality of slots, selecting the tattoo machine setting associated with said slot for use by the tattoo machine.

4. The method according to claim 1, further comprising receiving user input for modifying the tattoo machine setting, when using a corresponding cartridge with said tattoo machine.

5. The method according to claim 1, further comprising upon the attachment of a tattoo needle cartridge to said slot of said plurality of slots, associating with said slot the tattoo machine setting, said setting being one most recently used by the tattoo machine.

6. The method according to claim 1, further comprising attaching or detaching a tattoo needle cartridge comprising a magnet to/from said slot of said plurality of slots.

7. A tattoo machine control system, comprising:
   a holding arrangement for storing tattoo needle cartridges; and
   a tattoo machine controller configured to control a tattoo machine based on a tattoo machine setting;
   wherein said holding arrangement has a plurality of slots, each slot being arranged for receiving a respective tattoo needle cartridge, and
   wherein said system is configured to store a plurality of tattoo machine settings for said tattoo machine, wherein each tattoo machine setting of said plurality of tattoo machine settings corresponds to each respective slot of said plurality of slots.

8. The system according to claim 7, further comprising a detector for automatically detecting removal of a tattoo needle cartridge from said slot of said plurality of slots or attachment of a tattoo needle cartridge to said slot of said plurality of slots.

9. The system according to claim 8, wherein said detector comprises an inductive presence sensor.

10. The system according to claim 8, further configured to, upon said detector detecting the removal of a tattoo needle cartridge from a slot of said plurality of slots, select a tattoo machine setting associated with said slot for use by said tattoo machine.

11. The system according to claim 8, further configured to, upon said detector detecting the attachment of a tattoo needle cartridge to said slot of said plurality of slots, associate a tattoo machine setting used by said controller, said setting being one last used by said controller, with said slot.

12. The system according to claim 7, further comprising a user interface configured to allow a user to modify a tattoo machine setting by interacting with said controller.

13. The system according to claim 7, wherein said slot of said plurality of slots is provided with a magnet for holding a respective cartridge.

14. The system according to claim 7, wherein said control system comprises a tattoo machine controller unit separate from said holding arrangement.

15. The system according to claim 7, wherein said holding arrangement is configured to hold said tattoo needle cartridges at an end of said cartridges opposite to a needle nozzle of said cartridges.

16. A tattoo needle cartridge in combination with the system of claim 7, comprising a magnet configured to attach to a slot of said plurality of slots.

17. The tattoo needle cartridge according to claim 16, configured to fit the slot, wherein an interface between said cartridge and said slot is a flat surface.

18. The tattoo needle cartridge according to claim 16, wherein said magnet is a drive magnet connected to a tattoo needle.

19. The tattoo needle cartridge according to claim 16, comprising a rigid back wall.

20. The tattoo needle cartridge according to claim 16, configured for radial magnetic engagement with a tattoo machine drive unit.

* * * * *